United States Patent [19]

Wallace

[11] Patent Number: Plant 5,537

[45] Date of Patent: Aug. 20, 1985

[54] HYBRID CHESTNUT TREE 'REVIVAL'

[76] Inventor: Robert D. Wallace, Rte. 3, Box 267, Alachua, Fla. 32615

[21] Appl. No.: 548,761

[22] Filed: Nov. 4, 1983

[51] Int. Cl.[3] ..... A01H 5/00

[52] U.S. Cl. ..... Plt./30

[58] Field of Search ..... Plt./30

*Primary Examiner*—James R. Feyrer

[57] ABSTRACT

A medium size, vigorous chestnut tree, having a single, upright straight bole and dense foliage with heavily scented flowers appearing after leaf out in spring; the tree being a regular (yearly) and prolific bearer of very large and very sweet nuts, the burrs cracking in mid-September; the tree also showing all evidence of having a very high inherent resistance to the chestnut bark blight (*Endothia parasitica*), coming from a line of hybrid chestnut trees that have not shown a single instance of infection in over 30 years of breeding efforts and passing inoculation tests without succumbing to infection, and the present variety itself not showing any instance of blight intrusion in 7 years of growth in the orchard.

1 Drawing Figure

ORIGIN OF THE VARIETY

The present variety is an open-pollinated seedling, specially selected, from $F_2$ generation American X Chinese chestnut hybrid (unpatented) growing in the Chestnut Hill Nursery Orchards in Alachua, Fla. The unpatented $F_2$ hybrid trees originated in a cross made by my grandfather, Dr. Robert T. Dunstan, between flowering grafts of an exceptional uninfected native American chestnut (unpatented) found in a grove of dead and dying chestnuts, and a composite tree of 3 USDA released varieties of Chinese chestnut, Kuling, Meiling, and Nanking (all unpatented), in 1953 in North Carolina. Seedlings from the first cross were raised to flowering and then pollinated in a backcross to the American parent tree. The resultant $F_2$ generation was set out in the Chestnut Hill orchard where it exists today in excellent health. In continuation of the selection process, nuts from the $F_2$ trees bearing the largest quantity of largest and sweetest nuts were planted. These seedlings ($F_3$ generation) were raised in the nursery and then set out in the orchard. The present variety is the individual $F_3$ seedling tree, exhibiting the finest of qualities in nut size, taste and production that I have determined to be novel and distinct.

ASEXUAL REPRODUCTION OF THE VARIETY

The present variety having exceptional characteristics, was asexually reproduced by myself by grafting on to Chinese chestnut rootstocks (unpatented). In maturity, all such reproductions run true to the original tree in all respects.

SUMMARY OF THE VARIETY

The present variety of chestnut tree is of medium size, vigorous in growth, of characteristic upright form, with branches spreading in the upper reaches of the tree, having large, oblong leaves with a dentate margin, flowering late but abundantly after leafing out; the tree bearing early and regularly every year, is a productive bearer of large reddish brown nuts, 2–3 per burr, the burrs cracking in mid-September to early October, the nuts easily released for harvesting. The pellicle is thin and the meat is cream colored and very sweet, and excellent in taste, even raw. The nuts are larger than even Chinese chestnuts and never bland or bitter in taste. The trees provide an excellent food source for man, livestock and wildlife.

The present variety is characterized by cold hardiness, yet capable of growing well and producing nuts as far south as north central Florida. The tree is particularly suited for orchard or homestead plantings, and because of the vigorous, timber type growth habit, excellent for use in woodlot production or reforestation projects to reclaim old land.

The present variety is most importantly characterized by coming from a line of chestnuts that in 30 years of propagation and growth, have never had a single instance of blight infection by *Endothia parasitica,* the fungus responsible for destroying the entire chestnut population of the United States. Constantly exposed to local blight populations, all injuries to the trees (such as sunburn) have healed without infection. Twenty-four grafted $F_2$ hybrid chestnuts (unpatented) were inoculated with fungal spores and mycelia and watched for one year; the fungus survived the incubation period and sustained limited bark intrusion on several individuals, yet in no case was there any girdling or fungally induced death of the trees. In almost all cases, inoculation sites healed over completely. The present variety itself has not shown any blight infection in over 7 years of growth in the orchard, in which there is a blighted American Chestnut growing less than 50 feet away.

BRIEF DESCRIPTION OF THE DRAWING

The drawing is an illustration, by photographic reproduction in color, of a twig with leaves and burrs and nuts out of the burrs.

DESCRIPTION OF THE VARIETY

The botanical details of this new and distinct variety of chestnut tree—with color definitions (except those in common color terms) referenced to *Maerz and Paul Dictionary of Color*— are as follows:

Tree:

*Size (at maturity).*—Large.

*Vigor.*—Very vigorous.

Trunk:

*Form.*—Upright with branches spreading in upper reaches of tree.
*Texture.*—Relatively smooth.
*Color of bark.*—Silvergray (13-A-1).

Branches:
*Form.*—Strong.
*Texture.*—Relatively smooth.
*Lenticels.*—Few, small.
*Branching habit.*—Spreading in upper region of tree.
*Color.*—New wood: Reddish brown and glossy. Mature wood: Silvery gray.

Foliage:
*Quantity.*—Abundant.
*Density.*—Dense.

Leaves:
*Size.*—Large. Average length — 5–7" (including petiole). Average width — 2".
*Shape.*—Oblong with acute tip and rounded base.
*Thickness.*—Thick.
*Texture.*—Smooth.
*Margin.*—Dentate.
*Petiole.*—Length: Medium. Thickness: Medium.
*Color.*—Top side — Glossy dark green (22-L-12). Under side — Lighter green (21-D-7).

Bloom:
*Amount of bloom.*—Heavy.
*Color.*—Creamy white (17-B-1).
*Blooming period.*—Late. After leaf out in April.
*Age at which tree starts flowering.*—Early; 2–3 years after graft placement.

Crop:
*Bearing.*—Regular (yearly) bearer.
*Productivity.*—Prolific.
*Ripening period.*—Short. September 15–October 1.
*Distribution of nuts on tree.*—Well distributed.
*Tenacity.*—Burrs crack while on tree and nuts easily released, many falling by themselves.

Hull:
*Description.*—Spiney, round burr.
*Size.*—3–4" In diameter.
*Number of nuts.*—2–3 Per burr.

*Dehiscence.*—Splits easily when still on tree. Some entire burrs split and fall to ground.
*Color.*—Brown (15-A-8).

Nut:
*Size.*—Large. Average size — $1\frac{1}{8}'' \times 1\frac{1}{8}'' \times 1''$ thick. Average weight — 24–32 nuts per pound.
*Form.*—Broad and ovoid on one side, flat on other side.
*Blossom end.*—Pointed tip.
*Basal end.*—Flattened.
*Color.*—India Red (7-L-6).
*Shell.*—Thin.
*Hardness of shell.*—Relatively hard, yet not rigid.
*Texture of shell.*—Smooth.
*Percentage of kernel to nut.*—Very high (95%).

Kernel:
*Size.*—Almost as large as nut size.
*Form.*—Same as nut shape.
*Pellicle.*—Thin.
*Flavor.*—Excellent. Very sweet.
*Color.*—Oyster white (10-B-1).

Resistance to insects: No unusual susceptibilities noted.
Resistance to disease: Very high inherent resistance to chestnut bark fungus (*Endothia parasitica*), no other susceptibilities to any other disease.

The chestnut tree and its nuts herein described may vary in slight detail due to climatic and soil conditions under which the variety may be grown; the present description being of the variety as grown in Alachua, Fla.

I claim:

1. A new and distinct variety of Chestnut tree, substantially as illustrated and described, which is of medium size, vigorous, upright, with abundant foliage and large, glossy, elliptical leaves with dentate margins and late (post leaf appearance) flowering; the tree being a regular and heavy bearer of large and very sweet nuts in burrs that crack in mid-September and release the crop easily; the trees being especially characterized by a very high inherent resistance to the chestnut bark blight.

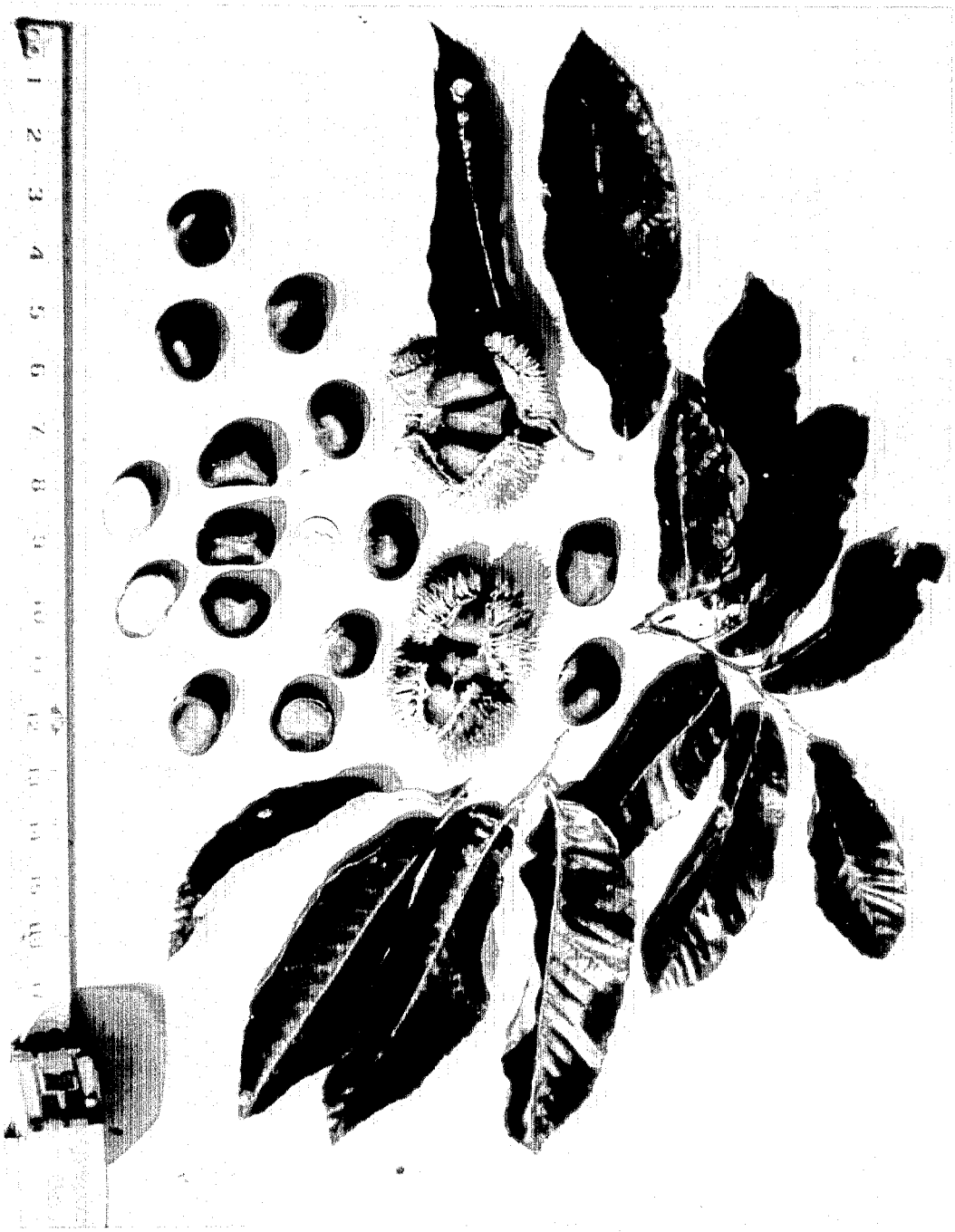

* * * * *